United States Patent [19]

Böttcher et al.

[11] Patent Number: 5,227,386
[45] Date of Patent: Jul. 13, 1993

[54] INDOLE DERIVATIVES

[75] Inventors: Henning Böttcher, Darmstadt;
Christoph Seyfried, Jugenheim;
Klaus-Otto Minck, Ober-Ramstadt;
Hans-Peter Wolf, Alsbach, all of
Fed. Rep. of Germany

[73] Assignee: Merck Patent Gesellschaft mit
beschrankter Haftung, Darmstadt,
Fed. Rep. of Germany

[21] Appl. No.: 673,544

[22] Filed: Mar. 22, 1991

[30] Foreign Application Priority Data

Mar. 24, 1990 [DE] Fed. Rep. of Germany ....... 4009565

[51] Int. Cl.$^5$ ..................... A61K 31/44; C07D 453/02
[52] U.S. Cl. ...................................... 514/305; 546/133
[58] Field of Search ......................... 546/133; 514/305

[56] References Cited

PUBLICATIONS

J. Org. Chem. vol. 40, No. 17, 1975; pp. 2525-2529 "3-Cycloalkenylindoles" Kurt Freten.
J. Org. Chem. vol. 33, No. 2, Feb. 1968 "Indoles From O-Nitrostyrenes, Synthesis and Reactions of 2-Indolyl-4-Piperidylmethyl Ketone" pp. 487-490.
J. Org. Chem., vol. 38, No. 17 (1975) "Synthesis of –Monosubstituted Indoles" pp. 3004-3011.

Primary Examiner—Marianne M. Cintins
Assistant Examiner—Catherine Scalzo
Attorney, Agent, or Firm—Millen, White, Zelano & Branigan

[57] ABSTRACT 3-(3-Indolyl)quinuclidines for the formula I $$\text{Ind—R} \quad\quad\quad \text{I}$$

in which
Ind is a 3-indolyl group which is unsubstituted or monosubstituted to tetrasubstituted by $C_{1-4}$-alkyl, trifluoromethyl, $C_{1-4}$-alkoxy, $C_{1-4}$-alkylthio, fluorine, chlorine, hydroxyl, hydroxymethyl, $C_{6-10}$-aryloxy, $C_{7-11}$-aralkyloxy, $C_{1-5}$-acyloxy, $C_{6-10}$-aroyloxy, $C_{1-4}$-alkylsulfonyloxy, $C_{6-10}$-arylsulfonyloxy, carboxyl, $C_{1-4}$-alkoxycarbonyl and/or methylenedioxy and
R is 3-quinuclidinyl or 2,3-dehydro-3-quinuclidinyl, and their physiologically acceptable salts can be used as psychopharmaceuticals.

9 Claims, No Drawings

INDOLE DERIVATIVES

SUMMARY OF THE INVENTION

The invention relates to novel 3-(3-indolyl)quinuclidine derivatives of the formula I Ind—R  I in which Ind is a 3-indolyl group which is unsubstituted or monosubstituted to tetrasubstituted by $C_{1-4}$-alkyl, trifluoromethyl, $C_{1-4}$-alkoxy, $C_{1-4}$-alkylthio, fluorine, chlorine, hydroxyl, hydroxymethyl, $C_{6-10}$-aryloxy, $C_{7-11}$-aralkyloxy, $C_{1-5}$-acyloxy, $C_{6-10}$-aroyloxy, $C_{1-4}$-alkylsulfonyloxy, $C_{6-10}$-arylsulfonyloxy, carboxyl, $C_{1-4}$-alkoxycarbonyl and/or methylenedioxy and R is 3-quinuclidinyl or 2,3-dehydro-3-quinuclidinyl, and their salts.

The invention has as one object providing novel compounds which can be used for the preparation of medicaments.

It has been found that the said substances have useful pharmacological properties combined with good tolerability. These effects make it possible to employ these substances for the treatment of disorders which are characterised by an excess of circulating serotonin or by a serotonergic hyperactivity. These include, in particular, the treatment of psychoses, of nausea and vomiting (as occurs, for example, in the chemotherapeutic or radiotherapeutic treatment of carcinoses), of dementia or other cognitive disorders, of migraine and of addictive disorders. These furthermore include use as an axiolytic, as an anti-aggressive, as an anti-depressive and as an analgesic. In particular, the compounds antagonise the effect of serotonin on 5-HT$_3$ receptors, such as, for example, the von Bezold-Jarisch reflex caused by serotonin (for method see J. Pharm. Pharmacol. 40 (1980), 301–302 and Nature 316 (1985), 126–131). Additionally, the novel compounds displace the substance $^3$H-GR65630, which is known as a selective 5-HT$_3$ ligand, from homogenised tissue from the endorhinal cortex of the rat (see Europ. J. Pharmacol. 159 (1989), 157–164).

The compounds I and their physiologically acceptable acid addition salts can therefore be used as medicament active compounds and also as intermediates for the preparation of other medically active compounds.

Similar compounds are described in J. Org. Chem. 40, 2525–2529 (1975), in J. Org. Chem. 38, 3004–3011 (1973) and in J. Org. Chem. 33, 487–490 (1968). However, in all these cases no pharmacological effects are indicated.

In the radical Ind, $C_{1-4}$-alkyl is preferably methyl, additionally also ethyl, n-propyl, isopropyl, n-butyl, isobutyl, sec.-butyl or tert.-butyl. $C_{1-4}$-alkoxy is preferably methoxy, additionally also ethoxy, n-propoxy, isopropoxy, n-butoxy, isobutoxy, sec.-butoxy or tert.-butoxy and $C_{1-5}$-acyloxy is preferably alkanoyl, e.g., formyloxy or acetyloxy, propanoyloxy, n-butanoyloxy, isobutanoyloxy or pivaloyloxy. $C_{1-4}$-alkylsulfonyloxy is preferably methanesulfonyloxy. $C_{1-6}$-aryloxy is preferably phenyloxy, $C_{7-11}$-aralkyloxy is preferably benzyloxy and $C_{6-10}$-aroyloxy is preferably benzoyloxy.

The radical Ind is preferably an unsubstituted, monosubstituted or disubstituted 3-indolyl group. If Ind is a substituted 3-indolyl group, it is preferably substituted in the 2-, 5- and/or 6-position and/or alkylated in the 1-position. In particular, Ind is preferably 3-indolyl, 5-benzyloxy-3-indolyl, 5-hydroxy-3-indolyl and 5-methoxy-2-methyl-3-indolyl. The radical R is preferably 3-quinuclidinyl.

The invention further relates to a process for the preparation of compounds of the formula I and of their salts, characterised in that compounds of the formula II Ind—H  II where Ind has the meaning indicated, are reacted with 3-quinuclidinone or one of its salts to give the 2,3-dehydro-3-quinuclidinyl compound (I, R=2,3-dehydro-3-quinuclidinyl) and this is reduced, if desired, to the 3-quinuclidinyl compound (I, R=3-quinuclidinyl), and/or a compound which otherwise corresponds to the formula I, but contains a removable protecting group instead of one or more H atoms, is converted into a compound of the formula I by removing this protecting group and/or a radical Ind in a compound of the formula I is converted into another radical Ind and/or a base of the formula I is converted into one of its salts by treating with an acid and/or a base of the formula I is liberated from a salt by means of a strong base.

The compound of the formula I is otherwise prepared by methods which are known per se, as are described in the literature (for example J. March, Advanced Organic Chemistry, 3rd Edition, John Wiley & Sons, New York or Houben-Weyl, Methoden der Organischen Chemie (Methods of Organic Chemistry), Georg-Thieme-Verlag, Stuttgart), and in particular under reaction conditions which are known and suitable for the said reactions. Use can also be made in this connection of variants which are known per se but which are not mentioned here in greater detail.

If desired, the starting materials for the claimed process can also be formed in situ such that they are not isolated from the reaction mixture, but directly reacted further to give a compound of the formula I.

A compound of the formula I (R=2,3-dehydro-3-quinuclidinyl) is preferably prepared by reacting a compound of the formula II and 3-quinuclidinone or one of its salts either in a basic medium or in an acidic medium at 40° to 120° C. The reaction time is preferably 2 to 60 hours.

For the alkaline medium, an inert water-miscible organic solvent is advantageously used together with aqueous KOH solution; particularly preferred organic solvents are lower alkanols, such as methanol or ethanol.

For reaction in acidic medium, a mixture of a water-miscible organic acid and an aqueous solution of an inorganic acid is preferably used; particularly preferred organic acids are lower carboxylic acids, such as acetic acid; phosphoric acid is preferred as an inorganic acid.

If desired, the resulting compound of the formula I (R=2,3-dehydro-3-quinuclidinyl) can then be reduced to the corresponding compound of the formula I (R=3-quinuclidinyl). For reduction, catalytic hydrogenations, preferably on a noble metal catalyst such as platinum oxide or palladium on carbon, in an inert solvent such as methanol, ethanol, tetrahydrofuran (THF) or ethyl acetate, at temperatures between 0° and 150° C., preferably between 10° and 80° C., and at pressures between 1 and 200, preferably 1 and 10 bar, are suitable.

The double bond can also be hydrogenated by means of diborane in THF. The diborane can be prepared in situ from sodium borohydride and boron trifluoride-ether complex.

The compounds of the formula I (R=3-quinuclidinyl) contain at least one asymmetric carbon atom. They can therefore exist as racemates if several asymmetric carbon atoms are present, and also as mixtures of several racemates and in various optically active forms.

The compounds of the formula II are known in some cases, see W. J. Houllhan, Indoles, Part I and II, Wiley Interscience, New York 1972; K. Freter, J. Org. Chem. 40, 2525–2529 (1975); R. J. Sundberg, The Chemistry of Indoles, Academic Press, New York, 1970; the unknown compounds can easily be prepared analogously to the known compounds. Thus, for example, N- or O-acylated compounds can be prepared from the non-acylated precursors by reaction with acid anhydrides, pyridine. for example acetic anhydride, in basic organic solvents, for example pyridine.

The protecting group can furthermore be removed from compounds which otherwise correspond to the formula I, but instead of one or more H atoms contain a removable protecting group, in particular a protecting group which can be removed by hydrogenolysis, such as benzyloxy, by means of catalytic hydrogenation, compounds of the formula I being obtained. Furthermore, particular compounds which otherwise correspond to the formula I, but instead of one or more H atoms contain a protecting group which can be removed by solvolysis, such as acyl (for example acetyl) or sulfonyl (for example methanesulfonyl or toluenesulfonyl) can be solvolyzed to give compounds of the formula I, in particular hydrolyzed.

The starting materials for the solvolysis are obtainable, for example, by reactions of 1-Z-Ind-H with 3-quinclidinone or one of its salts, Ind having the meaning indicated and Z being a group which can be removed by solvolysis. Thus, compounds of the formula I where the radical Ind in the 1-position of the indole contains an acyl group, preferably an alkanoyl, alkylsulfonyl or arylsulfonyl group in each case having up to 10 C atoms, such as methane-, benzene- or p-toluenesulfonyl, can in particular be hydrolysed to give the corresponding compounds which are unsubstituted in the 1-position, for example in acidic, or better, neutral or alkaline medium, at temperatures between 0° and 200° C. Bases used are advantageously sodium hydroxide, potassium hydroxide or calcium hydroxide, sodium carbonate or potassium carbonate or ammonia. The chosen solvent is preferably water, lower alcohols such as methanol or ethanol, ethers such as THF or dioxane, sulfones such as tetramethylene sulfone or their mixtures, particularly the mixtures containing water. Hydrolysis can even be carried out while treating with water alone, in particular at boiling heat.

A radical Ind in a compound of the formula I can be converted into another radical Ind by cleaving, for example, an ether group, the corresponding hydroxy derivative being formed, and/or esterifying a carboxyl group and/or saponifying an ester group and/or removing a carboxyl group by decarboxylation. Thus, the ether can be cleaved by treating with dimethyl sulfide-boron tribromide complex, for example in toluene, ethers such as THF or dimethyl sulfoxide, or by fusing with pyridine or aniline hydrohalides, preferably pyridine hydrochloride, at about 150°–250° C., or by treating with diisobutylaluminium hydride in toluene at about 0°–110° C., or by catalytic hydrogenation, for example in the presence of palladium-carbon in one of the abovementioned inert solvents, for example methanol, at, for example, 0° to 50° C. and at, for example, 1 to 10 bar. The said esterifications are carried out, for example, by the treatment of a solution of the carboxylic acid with an alcohol while adding $SOCl_2$ or a dehydrating agent, an excess of the alcohol preferably being used as solvent. Carboxylic acid esters are hydrolysed, for example, by means of acidic or basic catalysis in an aqueous solution which can additionally contain an inert water-miscible organic solvent, such as dioxane. Decarboxylations are advantageously carried out in alkaline medium, for example in N,N-dimethylaniline at temperatures between 40° and 190° C., preferably between 160° and 190° C.

A resulting base of the formula I can be converted into the respective acid addition salts using an acid. Acids which give physiologically acceptable salts are preferred for this reaction. Thus, inorganic acids can be used, for example sulfuric acid, hydrohalic acids such as hydrochloric acid or hydrobromic acid, phosphoric acids such as orthophosphoric acid, nitric acid, sulfaminic acid, and also organic acids, in particular aliphatic, alicyclic, araliphatic, aromatic or heterocyclic mono- or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- and ethanesulfonic acid, benzenesulfonic acid, p-toluenesulfonic acid, naphthalenemono- and -disulfonic acids, and laurylsulfuric acid. Acid addition salts which are not physiologically acceptable (for example picrates) can be used for the isolation and purification of the bases of the formula I.

If desired, a base of the formula I can be liberated from one of its salts using strong bases such as sodium hydroxide or potassium hydroxide, or sodium carbonate or potassium carbonate.

The invention further relates to the use of compounds of the formula I and/or their physiologically acceptable salts for the production of pharmaceutical preparations, in particular by non-chemical routes. In this connection, they can be brought into a suitable administration form together with at least one excipient or auxiliary and, if appropriate, in combination with one or more other active compound(s).

The invention further relates to compositions, in particular pharmaceutical preparations, containing one or more compounds of the formula I and/or their physiologically acceptable salts. These preparations can be employed as medicaments in human and veterinary medicine. Suitable excipients are organic or inorganic substances which are suitable for enteral (for example oral), parenteral or topical administration and do not react with the novel compounds, for example water, vegetable oils, benzyl alcohols, polyethylene glycols, gelatine, carbohydrates such as lactose or starch, magnesium stearate, talc or petroleum jelly. Tablets, coated tablets, capsules, syrups, elixirs, drops or suppositories are used in particular for enteral administration, solutions, preferably oily or aqueous solutions, and also suspensions, emulsions or implants are used for parenteral administration, and ointments, creams, plasters or powders are used for topical administration. The novel compounds can also be lyophilised and the resulting lyophilisates used, for example, for the production of injection preparations.

The preparations indicated can be sterilised and/or contain auxiliaries such as lubricants, preservatives, stabilisers and/or wetting agents, emulsifiers, salts for influencing the osmotic pressure, buffer substances, colorants, flavorings and/or aromatisers. If desired, they can also contain one or more other active compounds, for example one or more vitamins.

Compounds of the formula I and their physiologically acceptable salts can be used in the therapeutic treatment of the human or animal body and in controlling diseases, in particular diseases which are characterised by an excess of circulating serotonin or by a serotonergic hyperactivity. These diseases in particular include psychoses, nausea and vomiting, which arise as accompanying symptoms in the chemotherapeutic and radiotherapeutic treatment of tumors, dementia and other cognitive disorders, migraine and addictive disorders. Examples of addictive and cognitive disorders are:
addictive: cocaine and opiate abuse and withdrawal symptoms in connection with these diseases,
cognitive: presenile dementia of Alzheimer type disease, multiinfarct dementia.

The substances according to the invention are in this case as a rule administered in analogy to known commercially available preparations (thioridazine, haloperidol), preferably in dosages between about 0.2 and 1,000 mg, in particular between 0.2 and 100 mg per dosage unit. The daily dosage is preferably between about 0.003 and 20 mg/kg of body weight. However, the specific dose for each individual patient depends on the most diverse factors, for example on the activity of the specific compound employed, on the age, body weight, general state of health, sex, on the diet, on the time and route of administration, and on the excretion rate, medicament combination and severity of the particular disorder to which the therapy applies. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 40 09 565.7, are hereby incorporated by reference.

In the examples below, "customary working up" means: water is added, if necessary, the mixture is extracted with ethyl acetate or ether and separated, the organic phase is dried over sodium sulfate and filtered, and the filtrate is evaporated and purified by chromatography on silica gel and/or by crystallization. Rf means, if not stated otherwise, the Rf value on silica using the eluent toluene/methanol/triethylamine (7:2:1).

EXAMPLES

Example 1

A solution of 2.2 g of KOH in 20 ml of water is added to a solution of 2.3 g of indole and 3.2 g of 3-quinuclidinone in 120 ml of methanol; this mixture is boiled for 16 hours. The methanol is distilled off, and water and ether are added to the oily residue, whereupon 3-(3-indolyl)-2,3-dehydroquinuclidine crystallises, m.p. 250° (decomposition); Rf 0.28.

The following compounds are obtained analogously:
3-(4-Methoxy-3-indolyl)-2,3-dehydroquinuclidine
3-(5-Methoxy-3-indolyl)-2,3-dehydroquinuclidine, m.p. 223°–224°
3-(5-Ethoxy-3-indolyl)-2,3-dehydroquinuclidine
3-(5-Propoxy-3-indolyl)-2,3-dehydroquinuclidine
3-(6-Methoxy-3-indolyl)-2,3-dehydroquinuclidine
3-(5,6-Dimethoxy-3-indolyl)-2,3-dehydroquinuclidine
3-(5,6-Methylenedioxy-3-indolyl)-2,3-dehydroquinuclidine, m.p. 280°–281°
3-(4,5,6-Trimethoxy-3-indolyl)-2,3-dehydroquinuclidine
3-(5-Methylthio-3-indolyl)-2,3-dehydroquinuclidine, m.p. 187°–189°
3-(5-Fluoro-3-indolyl)-2,3-dehydroquinuclidine
3-(5-Chloro-3-indolyl)-2,3-dehydroquinuclidine
3-(5-Trifluoromethyl-3-indolyl)-2,3-dehydroquinuclidine
3-(6-Chloro-5-methoxy-3-indolyl)-2,3-dehydroquinuclidine
3-(6-Methyl-3-indolyl)-2,3-dehydroquinuclidine
3-(6-Methoxy-1-methyl-3-indolyl)-2,3-dehydroquinuclidine
3-(6-Ethoxy-1-methyl-3-indolyl)-2,3-dehydroquinuclidine
3-(6-Propoxy-1-methyl-3-indolyl)-2,3-dehydroquinuclidine

Example 2

3.2 g of 5-Methoxy-2-methylindole are dissolved in 60 ml of acetic acid and heated to 70°; 4.8 g of 3-quinuclidinone hydrochloride and 14.5 ml of 2N phosphoric acid are then added. The reaction solution is kept at 65° for 20 hours, then poured into ice-water and rendered alkaline using an NaOH solution. The resulting precipitate is filtered off with suction and washed with water. After extraction (ether) and chromatography, the product is dissolved in ether and acidified with isopropanolic hydrochloric acid, 3-(5-methoxy-2-methyl-3-indolyl)-2,3-dehydroquinuclidine precipitating as the hydrochloride; m.p. 240.9°–241.5° (decomposition); Rf 0.28.

The following compounds are obtained analogously:
3-(2-Methyl-3-indolyl)-2,3-dehydroquinuclidine; Rf 0.20
3-(5-Ethoxy-2-methyl-3-indolyl)-2,3-dehydroquinuclidine
3-(5-Propoxy-2-methyl-3-indolyl)-2,3-dehydroquinuclidine
3-(6-Methoxy-2-methyl-3-indolyl)-2,3-dehydroquinuclidine
3-(5,6-Dimethoxy-2-methyl-3-indolyl)-2,3-dehydroquinuclidine
3-(5,6-Methylenedioxy-2-methyl-3-indolyl)-2,3-dehydroquinuclidine
3-(4,5,6,-Trimethoxy-2-methyl-3-indolyl)-2,3-dehydroquinuclidine
3-(5-Methylthio-2-methyl-3-indolyl)-2,3-dehydroquinuclidine
3-(5-Fluoro-2-methyl-3-indolyl)-2,3-dehydroquinuclidine
3-(5-Chloro-2-methyl-3-indolyl)-2,3-dehydroquinuclidine 3-(5-Trifluoromethyl-2-methyl-3-indolyl)-2,3-dehydroquinuclidine
3-(6-Chloro-5-methoxy-2-methyl-3-indolyl)-2,3-dehydroquinuclidine
3-(2,6-Dimethyl-3-indolyl)-2,3-dehydroquinuclidine
3-(5-Methoxy-1,2-dimethyl-3-indolyl)-2,3-dehydroquinuclidine, m.p. 140°–143°
3-(6-Ethoxy-1,2-dimethyl-3-indolyl)-2,3-dehydroquinuclidine
3-(6-Propoxy-1,2-dimethyl-3-indolyl)-2,3-dehydroquinuclidine Example 3

0.4 g of 3-(3-indolyl)-2,3-dehydroquinuclidine is dissolved in 30 ml of methanol and hydrogenated at 26° with 0.2 g of palladium-carbon (5%) until no further gas absorption takes place. The hydrogenation solution is concentrated and the oily residue is crystallised from toluene. 3-(3-indolyl)quinuclidine is formed, m.p. 213.8°–215.8°; Rf 0.02.

The following compounds are obtained analogously:
3-(4-Methoxy-3-indolyl)quinuclidine
3-(5-Methoxy-3-indolyl)quinuclidine, m.p. 193°–195°
3-(5-Ethoxy-3-indolyl)quinuclidine
3-(5-Propoxy-3-indolyl)quinuclidine
3-(6-Methoxy-3-indolyl)quinuclidine
3-(5,6-Dimethoxy-3-indolyl)quinuclidine
3-(5,6-Methylenedioxy-3-indolyl)quinuclidine, m.p. 243°–245°
3-(4,5,6-Trimethoxy-3-indolyl)quinuclidine
3-(5-Methylthio-3-indolyl)quinuclidine
3-(5-Fluoro-3-indolyl)quinuclidine
3-(5-Chloro-3-indolyl)quinuclidine
3-(5-Trifluoromethyl-3-indolyl)quinuclidine
3-(6-Chloro-5-methoxy-3-indolyl)quinuclidine
3-(6-Methyl-3-indolyl)quinuclidine
3-(6-Methoxy-1-methyl-3-indolyl)quinuclidine
3-(6-Ethoxy-1-methyl-3-indolyl)quinuclidine
3-(6-Propoxy-1-methyl-3-indolyl)quinuclidine
3-(2-Methyl-3-indolyl)quinuclidine, m.p. 206.8°–208.6°
3-(5-Methoxy-2-methyl-3-indolyl)quinuclidine, hydrochloride, m.p. 231.7°–234.0°
3-(5-Ethoxy-2-methyl-3-indolyl)quinuclidine
3-(5-Propoxy-2-methyl-3-indolyl)quinuclidine
3-(6-Methoxy-2-methyl-3-indolyl)quinuclidine
3-(5,6-Dimethoxy-2-methyl-3-indolyl)quinuclidine
3-(5,6-Methylenedioxy-2-methyl-3-indolyl)quinuclidine
3-(4,5,6-Trimethoxy-2-methyl-3-indolyl)quinuclidine
3-(5-Methylthio-2-methyl-3-indolyl)quinuclidine
3-(5-Fluoro-2-methyl-3-indolyl)quinuclidine
3-(5-Chloro-2-methyl-3-indolyl)quinuclidine
3-(5-Trifluoromethyl-2-methyl-3-indolyl)quinuclidine
3-(6-Chloro-5-methoxy-2-methyl-3-indolyl)quinuclidine
3-(2,6-Dimethyl-3-indolyl)quinuclidine
3-(5-Methoxy-1,2-dimethyl-3-indolyl)quinuclidine, hydrochloride, m.p. 237°–238°
3-(6-Ethoxy-1,2-dimethyl-3-indolyl)quinuclidine
3-(6-Propoxy-1,2-dimethyl-3-indolyl)quinuclidine Example 4

4.5 g of 5-benzyloxyindole and 3.2 g of 3-quinuclidinone hydrochloride are dissolved in 120 ml of methanol, and a solution of 2.2 g of KOH in 20 ml of water is added. The mixture is boiled for 44 hours. The methanol is distilled off, and the residue is worked up as is customary. 3-(5-Benzyloxy-3-indolyl)-2,3-dehydroquinuclidine is obtained, m.p. 209.8°–210.5°; Rf 0.18.

The following compounds are obtained analogously:
3-(6-Benzyloxy-3-indolyl)-2,3-dehydroquinuclidine
3-(6-Benzyloxy-1-methyl-3-indolyl)-2,3-dehydroquinuclidine
3-(5-Benzyloxy-3-indolyl)-2,3-dehydroquinuclidine
3-(5-Benzyloxy-1-methyl-3-indolyl)-2,3-dehydroquinuclidine
3-(6-Benzyloxy-2-methyl-3-indolyl)-2,3-dehydroquinuclidine
3-(5-Benzyloxy-2-methyl-3-indolyl)-2,3-dehydroquinuclidine
3-(6-Benzyloxy-1,2-dimethyl-3-indolyl)-2,3-dehydroquinuclidine
3-(5-Benzyloxy-1,2-dimethyl-3-indolyl)-2,3-dehydroquinuclidine Example 5

0.7 g of 3-(5-Benzyloxy-3-indolyl)-2,3-dehydroquinuclidine is dissolved in 50 ml of methanol and hydrogenated at 21° with 1.0 g of palladium-carbon (5%) until no further gas absorption takes place. The hydrogenation solution is concentrated and the residue is dissolved in water and neutralised using NaOH. The precipitated 3-(5-Hydroxy-3-indolyl)quinuclidine is purified by chromatography, m.p. 280° (decomposition); Rf 0.2 (methanol/triethylamine; 8:2).

The following compounds are obtained analogously:
3-(6-Hydroxy-3-indolyl)quinuclidine
3-(6-Hydroxy-1-methyl-3-indolyl)quinuclidine
3-(5-Hydroxy-3-indolyl)quinuclidine
3-(5-Hydroxy-1-methyl-3-indolyl)quinuclidine
3-(6-Hydroxy-2-methyl-3-indolyl)quinuclidine
3-(5-Hydroxy-2-methyl-3-indolyl)-quinuclidine
3-(6-Hydroxy-1,2-dimethyl-3-indolyl)quinuclidine
3-(5-Hydroxy-1,2-dimethyl-3-indolyl)quinuclidine Example 6

200 mg of 3-(5-hydroxy-3-indolyl)quinuclidine are dissolved in 10 ml of pyridine and 5 ml of acetic anhydride are added with cooling. After one hour, the mixture is worked up as is customary. 3-(5-acetoxy-3-indolyl)quinuclidine is obtained.

The following compounds are obtained analogously:
3-(5-Pivaloyloxy-3-indolyl)quinuclidine
3-(5-Propanoyloxy-3-indolyl)quinuclidine
3-(5-Butanoyloxy-3-indolyl)quinuclidine
3-(5-Methanesulfonyloxy-3-indolyl)quinuclidine
3-(6-Acetoxy-3-indolyl)quinuclidine
3-(6-Pivaloyloxy-3-indolyl)quinuclidine
3-(6-Propanoyloxy-indolyl)quinuclidine
3-(6-(Butanoyloxy-3-indolyl)quinuclidine
3-(6-Methanesulfonyloxy-3-indolyl)quinuclidine
3-(5-Acetoxy-2-methyl-3-indolyl)quinuclidine
3-(5-Pivaloyloxy-2-methyl-3-indolyl)quinuclidine
3-(5-Propanoyloxy-2-methyl-3-indolyl)quinuclidine
3-(5-Butanoyloxy-2-methyl-3-indolyl)quinuclidine
3-(5-Methanesulfonyloxy-2-methyl-3-indolyl)quinuclidine
3-(6-Acetoxy-2-methyl-3-indolyl)quinuclidine
3-(6-Pivaloyloxy-2-methyl-3-indolyl)quinuclidine
3-(6-Propanoyloxy-2-methyl-3-indolyl)quinuclidine
3-(6-Butanoyloxy-2-methyl-3-indolyl)quinuclidine
3-(6-Methanesulfonyloxy-2-methyl-3-indolyl)quinuclidine Example 7

200 mg of 3-(1-Acetyl-5-methoxy-2-methyl-3-indolyl)quinuclidine are stirred on a steam bath for 16 hours with 100 mg of KOH in 7 ml of water and 14 ml of ethanol. The mixture is then worked up as is customary. 3-(5-methoxy-2-methyl-3-indolyl)quinuclidine is obtained; hydrochloride, m.p. 231.7°–234.0°.

Example 8

100 mg of 3-(3-quinuclidinyl)-5-methoxyindole-2-carboxylic acid are stirred at 180° in N,N-dimethylaniline for 8 hours. The mixture is then worked up as is customary. 3-(5-methoxy-3-indolyl)quinuclidine is obtained.

Example 9

In analogy to Example 1,3-(6-hydroxymethyl-3-indolyl)-2,3-dehydroquinuclidine, m.p.>399°, is obtained with 6-hydroxymethylindole. Analogously, there are obtained with 4- and 5-hydroxymethyl-indole:
3-(4-hydroxymethyl-3-indolyl)-2,3-dehydroquinuclidine
3-(5-hydroxymethyl-3-indolyl)-2,3-dehydroquinuclidine.

Example 10

Analogously to Example 3, there are obtained by hydrogenation of the corresponding 2,3-dehydroquinuclidines:
3-(4-hydroxymethyl-3-indolyl)-quinuclidine
3-(5-hydroxymethyl-3-indolyl)-quinuclidine
3-(6-hydroxymethyl-3-indolyl)-quinuclidine, m.p. 248°–250°.

The examples below relate to pharmaceutical preparations which contain substances of the formula I or one of their acid addition salts:

Example A: tablets

A mixture of 1 kg of 3-(5-hydroxy-3-indolyl)quinuclidine hydrochloride, 4 kg of lactose, 1.2 kg of potato starch, 0.2 kg of talc and 0.1 kg of magnesium stearate is compressed in a customary manner to give tablets such that each tablet contains 10 mg of active compound.

Example B: coated tablets

Analogously to Example A, tablets are pressed and are then coated in a customary manner with a coating of sucrose, potato starch, talc, tragacanth and colorant.

Example C: capsules

Hard gelatin capsules are filled with 2 kg of 3-(5-hydroxy-3-indolyl)quinuclidine hydrochloride in a customary manner such that each capsule contains 20 mg of active compound.

Example D: ampoules

A solution of 1 kg of 3-(5-hydroxy-3-indolyl)quinuclidine hydrochloride in 60 l of double-distilled water is sterile filtered, poured into ampoules, lyophilised under sterile conditions and sterile sealed. Each ampoule contains 10 mg of active compound.

Tablets, coated tablets, capsules and ampoules which contain another compound of the formula I and/or one or more physiologically acceptable acid addition salts of a compound of the formula I can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 3-(3-indolyl)quinuclidine compound of formula I $$\text{Ind}—\text{R} \qquad \qquad \text{I}$$

wherein

Ind is a 3-indolyl group which is unsubstituted, independently monosubstituted, disubstituted, trisubstituted or tetrasubstituted by $C_{1-4}$-alkyl, trifluoromethyl, $C_{1-4}$-alkoxy, $C_{1-4}$-alkylthio, fluorine, chlorine, hydroxy, hydroxymethyl, phenoxy, $C_{7-11}$-phenylalkyloxy, $C_{1-5}$-acyloxy, benzoyloxy, $C_{1-4}$-alkylsulfonyloxy, phenylsulfonyloxy, carboxyl, $C_{1-4}$-alkoxycarbonyl or methylenedioxy and R is 3-quinuclidinyl or 2,3-dehydro-3-quinuclidinyl, or a physiologically acceptable salt thereof.

2. A compound according to claim 1, wherein Ind is 3-indolyl independently substituted by 1-4 of methyl, ethyl, propyl, butyl, methoxy, ethoxy, propoxy, butoxy, formyloxy, acetyloxy, propanoyloxy, butanoyloxy, pivaloyloxy, methanesulfonyloxy, phenyloxy, benzyloxy or benzoyloxy.

3. A pharmaceutical composition comprising a compound of claim 1 and a pharmaceutically acceptable carrier.

4. A pharmaceutical composition comprising a compound of claim 2 and a pharmaceutically acceptable carrier.

5. A method of treating indications characterized by excess circulating serotonin in a host in need of such treatment, comprising administering to said host an effective amount of a compound of claim 1.

6. A method for treating nausea, vomiting or psychoses characterized by excess blood serotonin levels in a host in need of such treatment, comprising administering to said host an effective amount of a compound of claim 1.

7. A method according to claim 6, wherein the nausea, vomiting or psychoses are caused by the chemotherapeutic or radiotherapeutic treatment of carcinoses.

8. A method according to claim 5, wherein the indications are dementia, migraine or addictive disorders.

9. A method for antagonizing the effect of serotonin on 5-$HT_3$ receptors or for displacing $^3H$-GR65630 from said receptors in a host, comprising administering to said host an effective amount of a compound of claim 1.

* * * * *